US012338835B1

(12) United States Patent
Andres et al.

(10) Patent No.: US 12,338,835 B1
(45) Date of Patent: Jun. 24, 2025

(54) FAN DIFFUSER ASSEMBLY AND METHOD

(71) Applicant: ScentAir Technologies, LLC, Charlotte, NC (US)

(72) Inventors: Logan T. Andres, Indian Trail, NC (US); Matthew L Browne, Gastonia, NC (US); Daniel J. Connors, Nokomis, FL (US)

(73) Assignee: ScentAir Technologies, LLC, Charlotte, NC (US)

( * ) Notice: Subject to any disclaimer, the term of this patent is extended or adjusted under 35 U.S.C. 154(b) by 347 days.

(21) Appl. No.: 17/744,095

(22) Filed: May 13, 2022

Related U.S. Application Data

(60) Provisional application No. 63/188,128, filed on May 13, 2021.

(51) Int. Cl.
*F04D 29/54* (2006.01)
*A61L 9/12* (2006.01)
(Continued)

(52) U.S. Cl.
CPC ............ *F04D 29/541* (2013.01); *A61L 9/122* (2013.01); *A61L 9/22* (2013.01); *B01D 46/0041* (2013.01);
(Continued)

(58) Field of Classification Search
None
See application file for complete search history.

(56) References Cited

U.S. PATENT DOCUMENTS 6,027,406 A * 2/2000 Yazici ................... F04D 29/663
55/467
7,651,077 B1 1/2010 Rosener et al.
(Continued)

FOREIGN PATENT DOCUMENTS

CN 108087313 A * 5/2018 ........... F04D 25/166
DE 29815783 U1 * 12/1998 ............. A61L 9/046
(Continued)

OTHER PUBLICATIONS

CN108087313A_ENG (Espacenent machine translation of Mei) (Year: 2018).*
(Continued)

*Primary Examiner* — Gabriel E Gitman
(74) *Attorney, Agent, or Firm* — Schwartz Law Firm, P.C.

(57) ABSTRACT

A fan diffuser assembly incorporates an inverted frustoconical base having a large diameter end and an opposing small diameter end. A housing is located over the frustoconical base, and has an intake end, side walls and an output end. The intake end is longitudinally spaced apart from the large diameter end of the frustoconical base and cooperates with the side walls of the housing to define an air intake of the fan diffuser assembly. An electric fan is located within the housing and is mounted adjacent the small diameter end of the frustoconical base. Operation of the electric fan generates a 360-degree laminar airflow through the air intake, along a tapering exterior of the frustoconical base, through the housing and outwardly through the output end into a surrounding environment. An air conditioning element is located inside the housing between the electric fan and the output end of the housing.

20 Claims, 9 Drawing Sheets

(51) Int. Cl.
*A61L 9/22* (2006.01)
*B01D 46/00* (2022.01)
*B03C 3/011* (2006.01)
*B03C 3/41* (2006.01)
*B03C 3/82* (2006.01)
*F04D 19/00* (2006.01)
*F04D 25/06* (2006.01)
*F04D 29/70* (2006.01)

(52) U.S. Cl.
CPC ............. *B03C 3/011* (2013.01); *B03C 3/41* (2013.01); *B03C 3/82* (2013.01); *F04D 19/002* (2013.01); *F04D 25/06* (2013.01); *F04D 29/703* (2013.01); *A61L 2209/133* (2013.01); *A61L 2209/15* (2013.01); *A61L 2209/16* (2013.01); *B03C 2201/06* (2013.01)

(56) References Cited

U.S. PATENT DOCUMENTS

| | | | |
|---|---|---|---|
| 8,564,924 | B1 | 10/2013 | Waddell et al. |
| 9,441,845 | B2 | 9/2016 | Waddell |
| 9,509,125 | B2 | 11/2016 | Waddell et al. |
| 9,925,567 | B2 | 3/2018 | Waddell |
| 10,020,180 | B2 | 7/2018 | Waddell |
| 10,128,075 | B2 | 11/2018 | Waddell |
| 10,319,569 | B2 | 6/2019 | Waddell |
| 11,283,245 | B2 | 3/2022 | Waddell |
| 2004/0202541 | A1* | 10/2004 | Stewart ................. F04D 29/601 415/213.1 |
| 2021/0080130 | A1* | 3/2021 | Shimizu ................. B01D 46/10 |
| 2021/0236978 | A1* | 8/2021 | Smith ................... B01D 46/12 |
| 2022/0018552 | A1* | 1/2022 | Karamanos ........... F24F 13/062 |
| 2022/0088260 | A1* | 3/2022 | Krigmont ............. A61L 9/032 |

FOREIGN PATENT DOCUMENTS

| | | | | |
|---|---|---|---|---|
| KR | 20100056797 | A | * | 5/2010 |
| KR | 20140025845 | A | * | 3/2014 ............. B01D 46/00 |
| WO | WO-9631741 | A1 | * | 10/1996 ............... A61L 9/03 |

OTHER PUBLICATIONS

KR20140025845A_ENG (Espacenent machine translation of Tang) (Year: 2014).*
WO9631741A1_ENG (Espacenent machine translation of Doerfel) (Year: 1996).*
KR20100056797A_ENG (Espacenent machine translation of Kim) (Year: 2010).*
DE29815783U1_ENG (Espacenet machine translation of Siegrist) (Year: 1998).*
KR20100056797A_ENG (Espacenet machine translation of Kim) (Year: 2010).*

* cited by examiner

FAN DIFFUSER ASSEMBLY AND METHOD

TECHNICAL FIELD AND BACKGROUND OF THE DISCLOSURE

The present disclosure relates broadly and generally to a fan diffuser assembly and method.

In exemplary embodiments, the invention comprises a commercial-grade scent/ionization unit designed to target spaces up to 1,000 square feet. The invention is engineered for flexible placement, and comprises a compact and lightweight system which can be positioned vertically, horizontally or wall mounted. In one implementation, the invention provides ultra-quiet fragrance diffusion and discreetly creates a fragrance experience for customers in a commercial or retail environment. The invention may be Wi-Fi and Bluetooth enabled for convenient control of targeted areas using software, hardware and firmware components. Access and control may also be managed remotely via an Internet web portal and cloud-based system management software.

In other exemplary embodiments, the present invention may comprise an ionization unit configured to deliver positive and negative ions into a surrounding environment. The invention may incorporate technology designed to reduce pathogens including SARS-CoV-2, and to remove irritants such as dust, dander or pollen, and VOCs (Volatile Organic Compounds) from the targeted space.

SUMMARY OF EXEMPLARY EMBODIMENTS

Various exemplary embodiments of the present disclosure are described below. Use of the term "exemplary" means illustrative or by way of example only, and any reference herein to "the invention" is not intended to restrict or limit the invention to exact features or steps of any one or more of the exemplary embodiments disclosed in the present specification. References to "exemplary embodiment," "one embodiment," "an embodiment," "various embodiments," and the like, may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

It is also noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

According to one exemplary embodiment, the present disclosure comprises a fan diffuser assembly and method. The exemplary fan diffuser assembly comprises an inverted frustoconical base having a large diameter end and an opposing small diameter end. A housing is located over the frustoconical base, and comprises an intake end, side walls and an output end. The intake end is (longitudinally) spaced apart from the large diameter end of the frustoconical base and cooperates with the side walls of the housing to define an air intake of the fan diffuser assembly. An electric fan is located within the housing and is mounted adjacent the small diameter end of the frustoconical base. Operation of the electric fan generates a 360-degree laminar airflow through the air intake, along a tapering exterior of the frustoconical base, through the housing and outwardly through the output end into a surrounding environment. An air conditioning element is located inside the housing between the electric fan and the output end of the housing.

The term "air conditioning element" refers broadly herein to any product, component or device intended for use in a fan diffuser assembly to condition a surrounding environment, including (e.g.) freshening, eliminating odors, filtering, purifying, reducing pathogens, removing irritants, and other such applications.

According to another exemplary embodiment, a cylindrical cartridge nest is located inside the housing between the electric fan and the output end of the housing.

According to another exemplary embodiment, the air conditioning element comprises an exchangeable fragrance cartridge configured for being carried within the cartridge nest inside the housing.

According to another exemplary embodiment, the air conditioning element comprises an ionization device.

According to another exemplary embodiment, the ionization device comprises a needlepoint bipolar ion generator.

According to another exemplary embodiment, a removable perforated grill is located at the output end of the housing.

According to another exemplary embodiment, the housing has a generally truncated pyramidal shape.

According to another exemplary embodiment, the intake end of the housing is rectangular.

According to another exemplary embodiment, the output end of the housing is rectangular.

According to another exemplary embodiment, the side walls of the housing are solid and continuous.

According to another exemplary embodiment, the frustoconical base further comprises a plurality of spaced apart assembly support posts extending from the large diameter end to the small diameter end.

According to another exemplary embodiment, an assembly mounting plate is located between the frustoconical base and the electric fan, and defines a circular plate opening corresponding to an axial diameter of the electric fan. The exemplary fan has a center hub and a plurality of attached identical blades. The "axial diameter" of the fan is a measurement of the length of a single fan blade, multiplied by 2, plus the diameter of the hub.

According to another exemplary embodiment, the housing comprises a plurality of interior corner mounts for attaching the assembly mounting plate using fasteners.

According to another exemplary embodiment, a diameter of the small diameter end of the frustoconical base end corresponds substantially to a hub diameter of the electric fan.

According to another exemplary embodiment, the large diameter end of the frustoconical base is greater than 3 times a diameter of the small diameter end of the frustoconical base.

According to another exemplary embodiment, a longitudinal distance between the large diameter end of the frustoconical base and the small diameter end of the frustoconical base is between 3-5 inches.

According to another exemplary embodiment, the tapered exterior of the frustoconical base between the large diameter end and the small diameter end has a curvature radius of between about 4-5 inches.

According to another exemplary embodiment, the electric fan of the diffuser assembly generates a volumetric airflow at a rate between 50 CFM and 100 CFM when incorporating the exchangeable fragrance cartridge, and up to 500 CFM when incorporating the ionization device.

BRIEF DESCRIPTION OF THE DRAWINGS

Exemplary embodiments of the present disclosure will hereinafter be described in conjunction with the following drawing figures, wherein like numerals denote like elements, and wherein.

DESCRIPTION OF EXEMPLARY EMBODIMENTS AND BEST MODE

The present invention is described more fully hereinafter with reference to the accompanying drawings, in which one or more exemplary embodiments of the invention are shown. Like numbers used herein refer to like elements throughout. This invention may, however, be embodied in many different forms and should not be construed as limited to the embodiments set forth herein; rather, these embodiments are provided so that this disclosure will be operative, enabling, and complete. Accordingly, the particular arrangements disclosed are meant to be illustrative only and not limiting as to the scope of the invention, which is to be given the full breadth of the appended claims and any and all equivalents thereof. Moreover, many embodiments, such as adaptations, variations, modifications, and equivalent arrangements, will be implicitly disclosed by the embodiments described herein and fall within the scope of the present invention.

Although specific terms are employed herein, they are used in a generic and descriptive sense only and not for purposes of limitation. Unless otherwise expressly defined herein, such terms are intended to be given their broad ordinary and customary meaning not inconsistent with that applicable in the relevant industry and without restriction to any specific embodiment hereinafter described. As used herein, the article "a" is intended to include one or more items. Where only one item is intended, the term "one", "single", or similar language is used. When used herein to join a list of items, the term "or" denotes at least one of the items, but does not exclude a plurality of items of the list.

For exemplary methods or processes of the invention, the sequence and/or arrangement of steps described herein are illustrative and not restrictive. Accordingly, it should be understood that, although steps of various processes or methods may be shown and described as being in a sequence or temporal arrangement, the steps of any such processes or methods are not limited to being carried out in any particular sequence or arrangement, absent an indication otherwise. Indeed, the steps in such processes or methods generally may be carried out in various different sequences and arrangements while still falling within the scope of the present invention.

Additionally, any references to advantages, benefits, unexpected results, or operability of the present invention are not intended as an affirmation that the invention has been previously reduced to practice or that any testing has been performed. Likewise, unless stated otherwise, use of verbs in the past tense (present perfect or preterit) is not intended to indicate or imply that the invention has been previously reduced to practice or that any testing has been performed.

Figure 1:
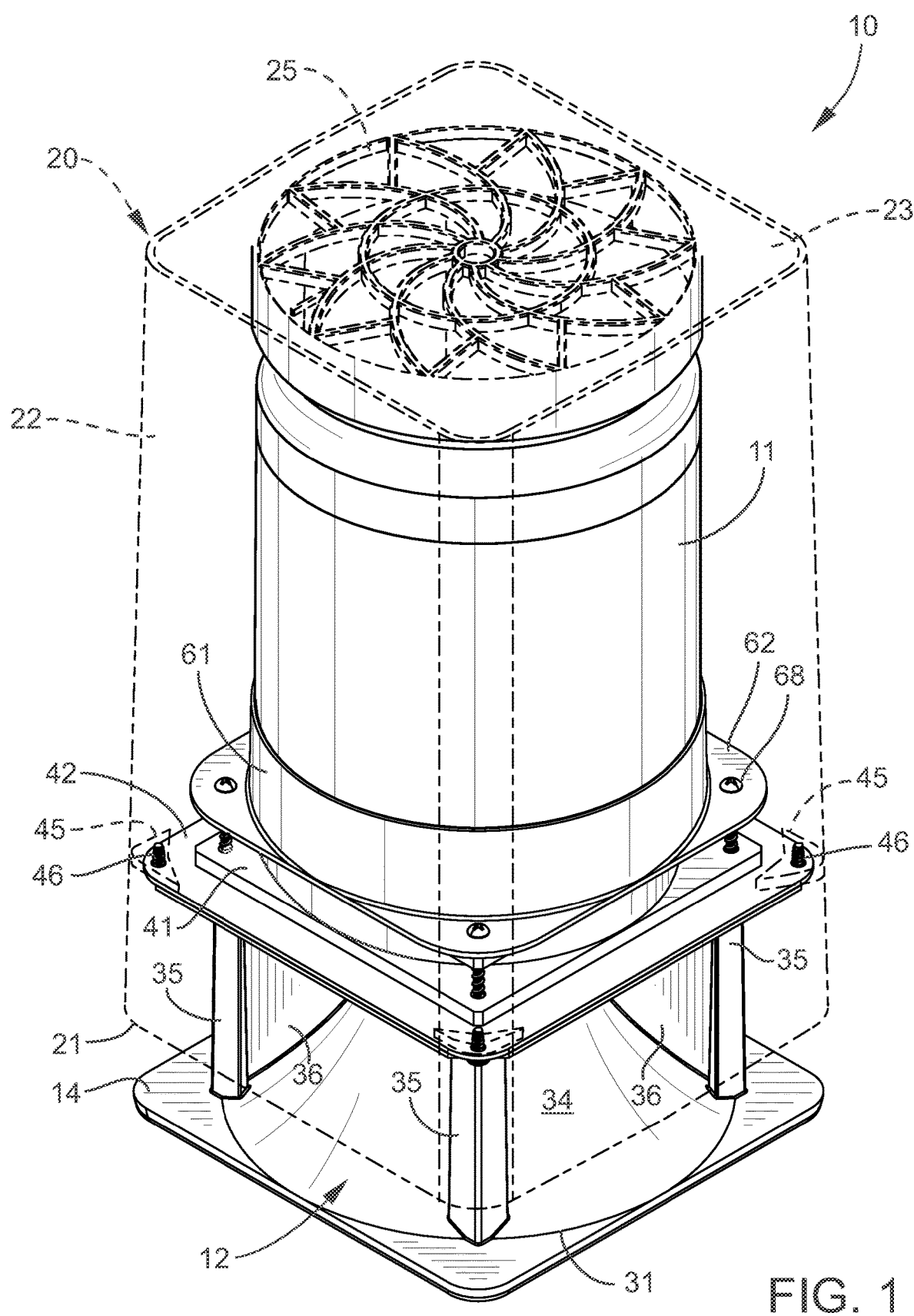
FIG. 1 is a perspective view of a fan diffuser assembly according to one exemplary embodiment of the present disclosure, and showing the exterior housing in phantom to better illustrate interior components of the assembly.
Figure 2:
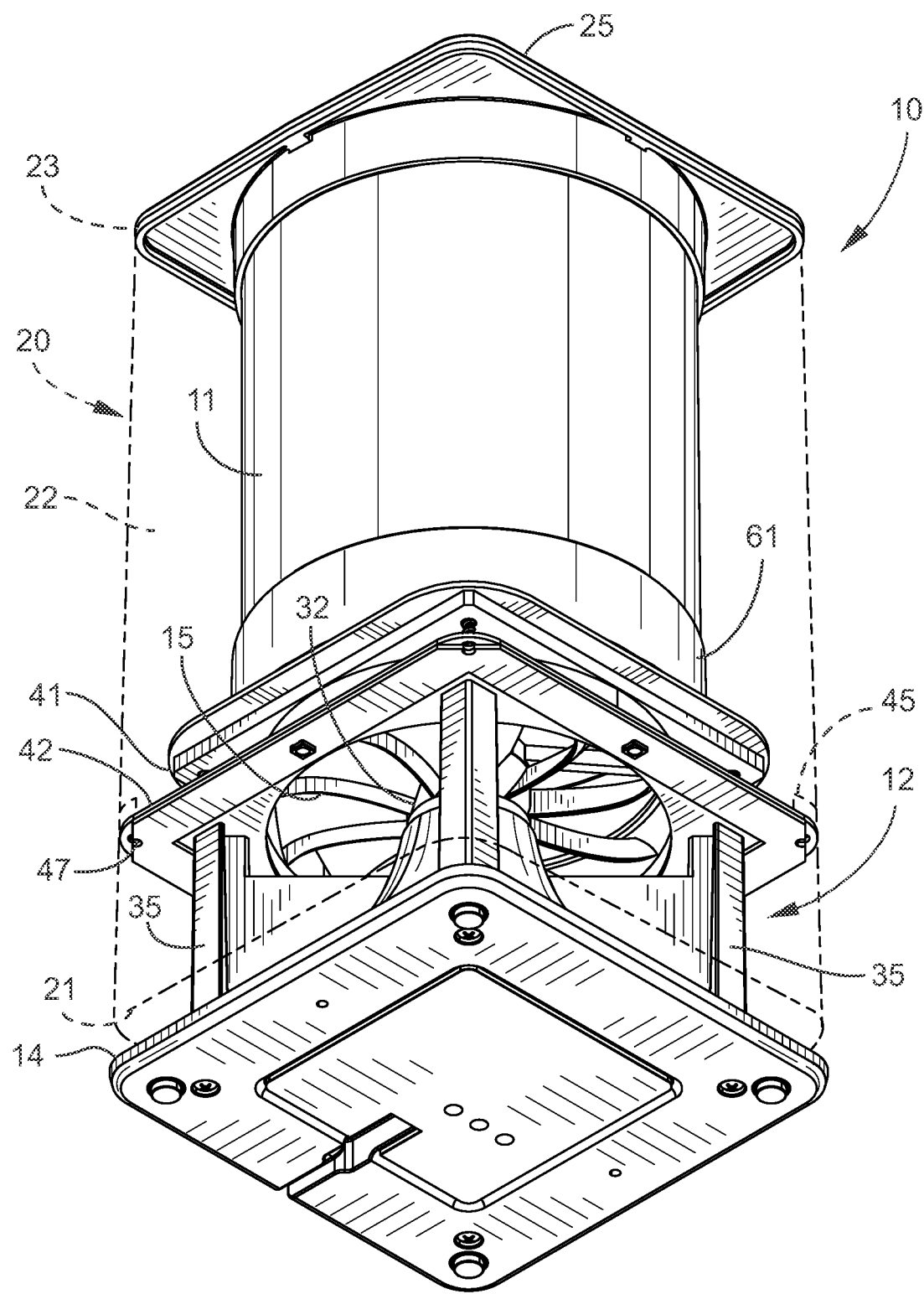
FIG. 2 is a further perspective view of the exemplary fan diffuser assembly.

Referring now specifically to the drawings, a fan diffuser assembly according to one exemplary embodiment of the present disclosure is illustrated in FIG. 1 and shown generally at broad reference numeral 10. The exemplary fan diffuser assembly 10 incorporates an air conditioning element 11 designed to modify the air in a surrounding targeted space. The assembly 10 can be placed upon or mounted to any flat surface including counter tops, elevated shelving, walls, floor and ceiling, and can be arranged in any desired orientation (e.g., horizontal or vertical) without impacting its output or performance. In exemplary applications, the assembly 10 is especially applicable for use in hotels and resorts, retail stores, restaurants, senior living facilities, business offices, casinos, and other enclosed commercial, industrial or residential locations targeting spaces up to 1,000 square feet and more.

In the embodiment of FIGS. 1-6, the air conditioning element 11 of the exemplary fan diffuser assembly 10 comprises an exchangeable fragrance cartridge. One prior art example of an exchangeable fragrance cartridge is disclosed in U.S. Pat. No. 7,651,077. The complete disclosure of this patent is incorporated herein by reference. In an alternative embodiment shown in FIGS. 7-10, the exemplary fan diffuser assembly 110 of the present disclosure incorporates an air conditioning element 111 comprising an ionization device. Prior art examples of ionization devices applicable in the present assembly are disclosed in U.S. Pat. Nos. 8,564,924, 9,441,845, 9,925,567, 10,319,569, 10,128,075, 10,020,180, and 11,283,245. The complete disclosures of these references are incorporated herein by reference.

Referring to FIGS. 1-6, the fan diffuser assembly 10 includes an inverted frustoconical base 12 with rectangular base plate 14, a high-speed electric fan 15, and the exchangeable fragrance cartridge (air conditioning element) 11 referenced above. An exterior housing 20 covers the electric fan 15 and fragrance cartridge 11, and has a generally truncated pyramidal shape including a large rectangular intake end 21, tapered side walls 22, and a smaller rectangular output end 23. The intake end 21 of the housing 20 is longitudinally spaced from the base plate 14 and cooperates with the side walls 22 and frustoconical base 12 to define an air intake of the fan diffuser assembly 10. A perforated grill 25 is located at the output end 23 of the housing 20. The exemplary grill 25 may be permanently attached to the housing 20 by adhesive, bonding agent, ultrasonic welding or the like, or may be removably attached using rare earth magnets or other suitable means.

As best shown in FIGS. 1, 2, 4 and 5, the exemplary frustoconical base 12 resides substantially within the exterior housing 20, and has opposing large and small diameter ends 31, 32, a tapering exterior 34 between the two ends 31, 32, and four circumferentially spaced assembly support posts 35. Each support post 35 extends longitudinally from the large diameter end 31 of the frustoconical base 12 to the small diameter end 32, and comprises an integrally formed radial web 36 for added stability and reinforcement. The large diameter end 31 of the frustoconical base 12 may be greater than 3 times a diameter of the small diameter end 32. In one exemplary embodiment, the diameter "D1" of the large diameter end 31 measures approximately 5.95 inches, while the diameter "D2" of the small diameter end 32 measures approximately 1.50 inches. In this embodiment, the longitudinal distance (or height) "H" between the ends 31, 32 is approximately 3.12 inches, and the curvature radius "R" of the tapering exterior 34 between the ends 31, 32 is approximately 4.74 inches. The tapering exterior 34 of the frustoconical base 12 accelerates laminar airflow and allows for lower overall placement of the electric fan 15 within the assembly 10 without reducing intake air volume or decreasing negative static pressure.

Figure 3:
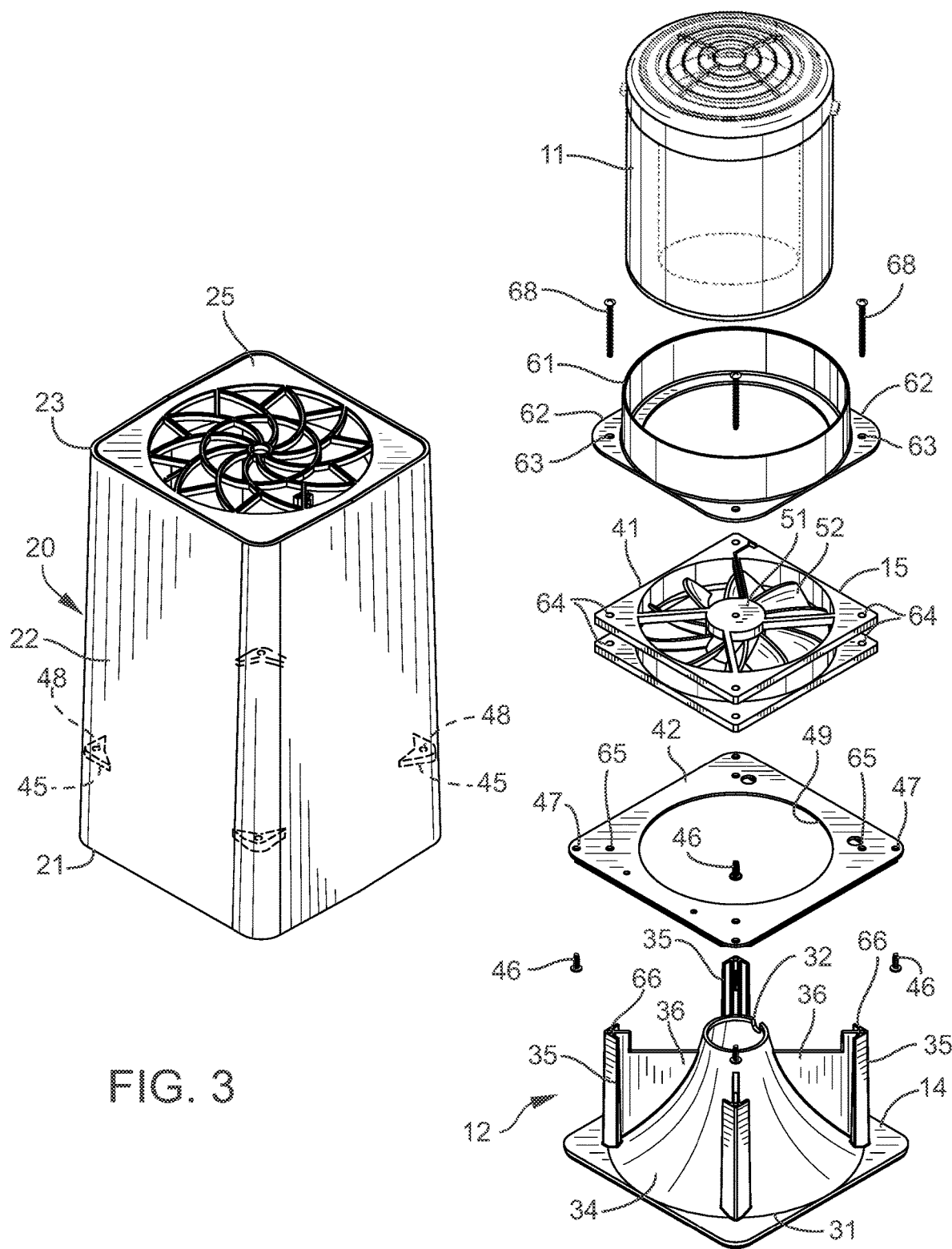
FIG. 3 is an exploded perspective view of the exemplary fan diffuser assembly.
Figure 4:
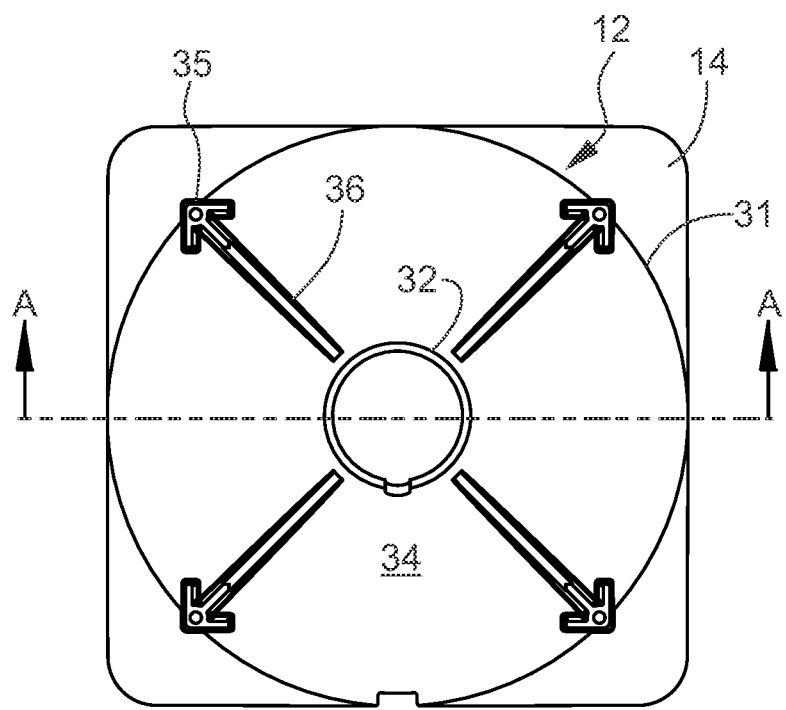
FIG. 4 is a plan view of the inverted frustoconical base of the exemplary fan diffuser assembly.
Figure 5:
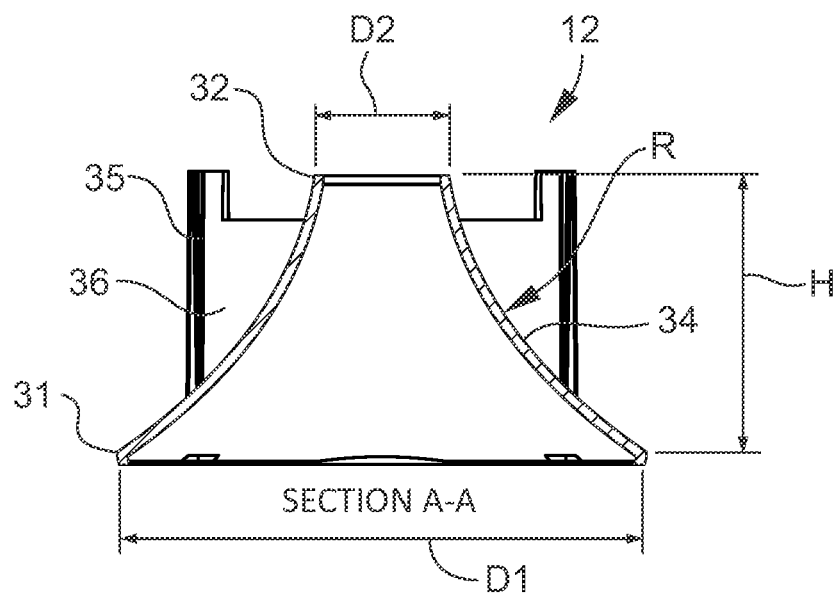
FIG. 5 is a cross-sectional view taken at line A-A of the frustoconical base shown in FIG. 4.
Figure 6:
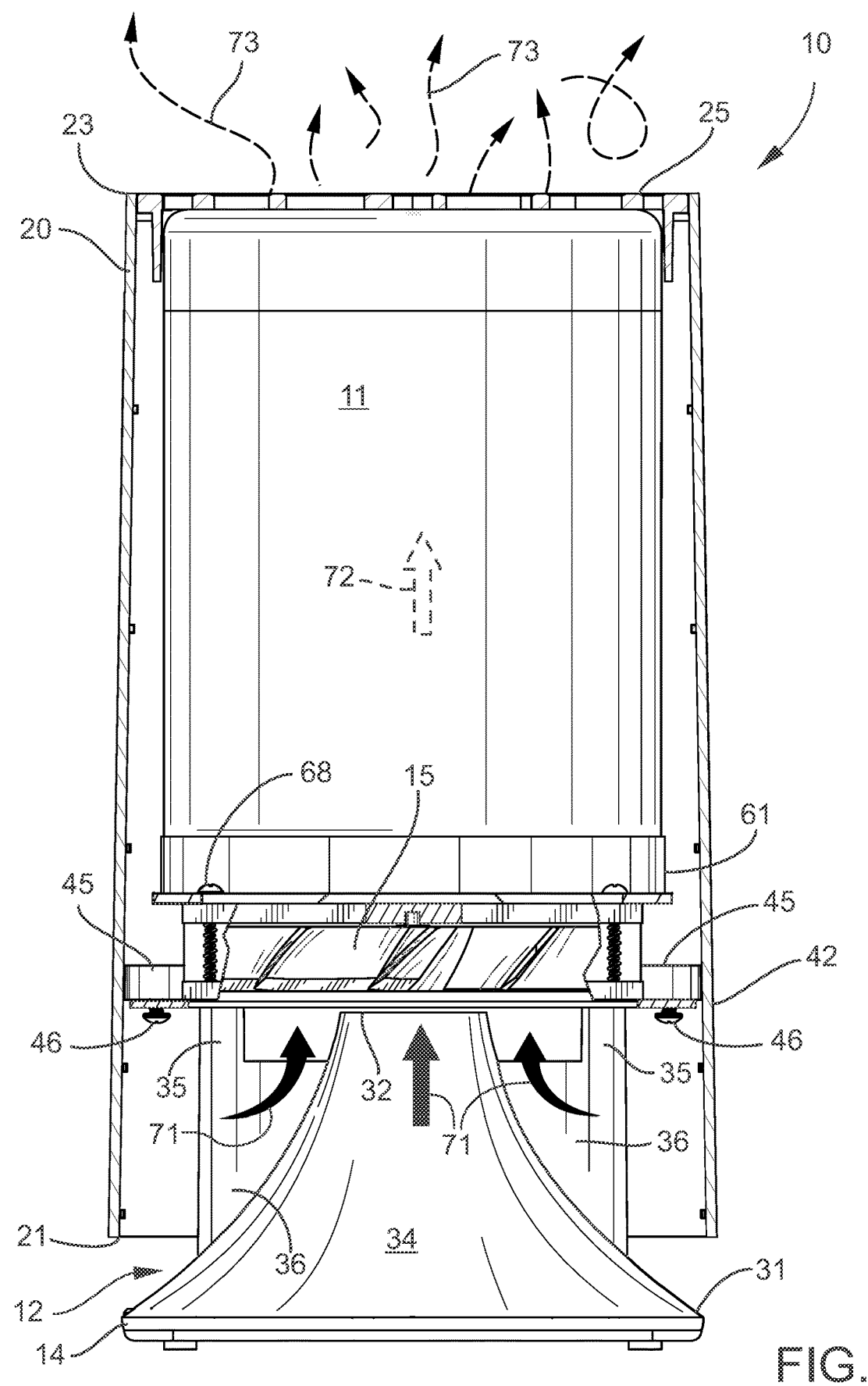
FIG. 6 is a side elevation of the exemplary fan diffuser assembly with parts shown in cross-section and direction arrows to demonstrate airflow into and through the assembly.
Figure 7:
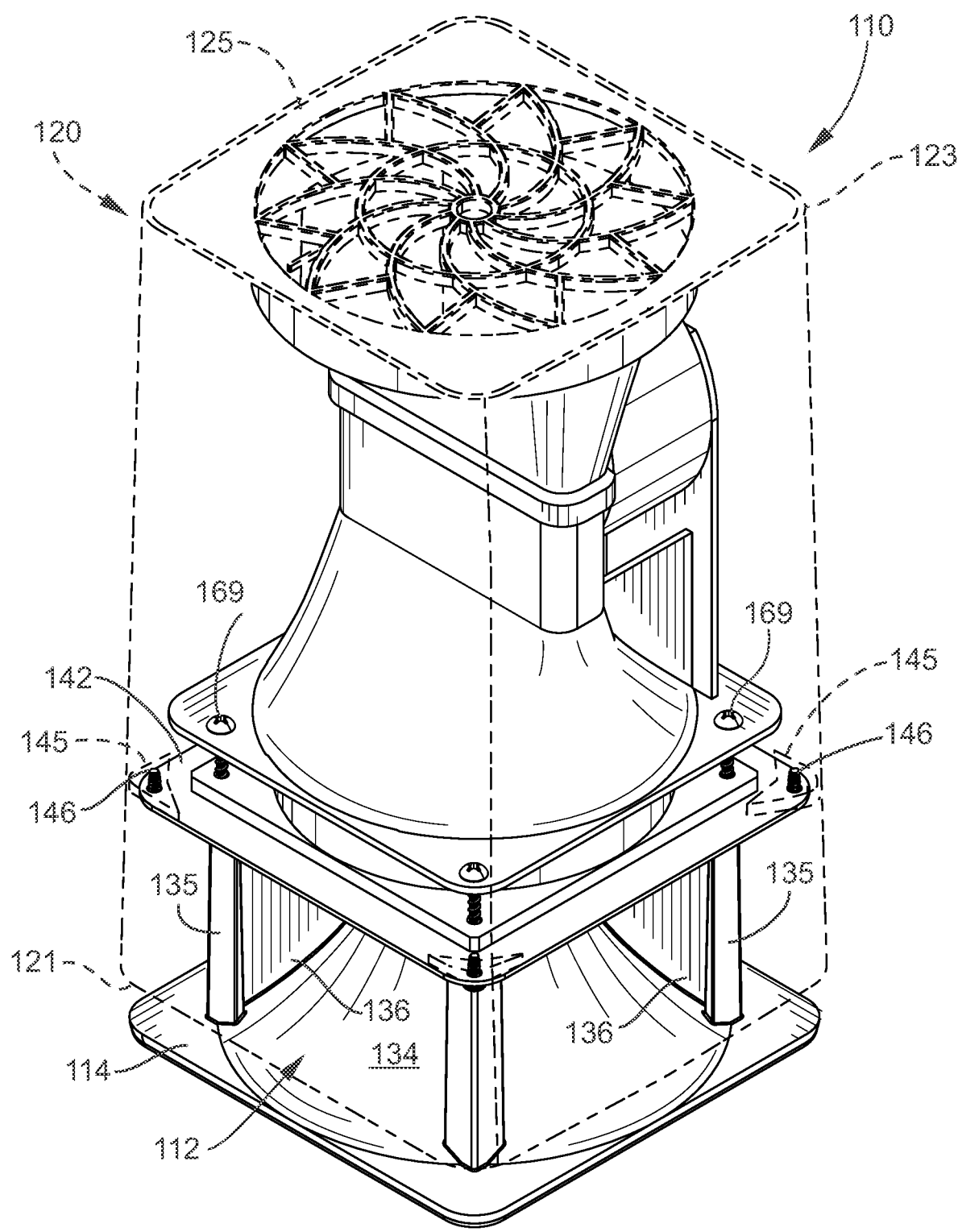
FIG. 7 is a perspective view of a fan diffuser assembly according to a second exemplary embodiment of the present disclosure, and showing the exterior housing in phantom to better illustrate interior components of the assembly.

Referring to FIGS. 1 and 3, the electric fan 15 is operatively held within a square frame 41 carried by an assembly mounting plate 42 located adjacent the small diameter end 32 of the frustoconical base 12. The assembly mounting plate 42 attaches to interior corner mounts 45 of the housing 20 using fasteners 46 through aligned holes 47 and 48, and defines a circular plate opening 49 of a size corresponding substantially to an axial diameter of the fan 15. The exemplary fan 15 comprises an electric motor (not shown), a rotatable center hub 51 and a number of attached blades 52. The center hub 51 longitudinally aligns with the small diameter end 32 of the frustoconical base 12, and has a diameter corresponding substantially to the diameter of end 32.

In the present embodiment, a cylindrical cartridge nest 61 is located inside the housing 20 between the electric fan 15 and the output end 23 of the housing 20. As best shown in FIGS. 1 and 3, the cartridge nest 61 has integrally formed mounting ears 62 with respective fastener holes 63 longitudinally aligned with corresponding fasteners holes 64, 65, 66 formed in the square frame 41 of fan 15, assembly mounting plate 42, and support posts 35. Respective fasteners 68 are inserted through the aligned holes 63-66 to join the assembled parts together. The exchangeable fragrance cartridge 11 is carried within the fragrance cartridge nest 61 inside the housing 20. As demonstrated in FIG. 6, when activated the electric fan 15 generates a 360-degree laminar airflow into and through the air intake of the diffuser assembly 10. The laminar airflow enters the housing 20 at intake end 21 and accelerates along the tapering exterior 34 of the frustoconical base 12, as indicated by direction arrows 71. The accelerated laminar airflow then passes through the rotating fan 15, through the exchangeable fragrance cartridge 11, as indicated by direction arrow 72, and outwardly in a more turbulent flow through the perforated grill 25, thereby releasing the selected fragrance into the surrounding environment as indicated by direction arrows 73. In the present diffuser assembly 10, the electric fan 15 generates a volumetric airflow of 60 CFM in one exemplary embodiment and 72 CFM in another exemplary embodiment. Intake airflow can be blocked on multiple sides of the assembly without effecting fan output or performance.

Referring now to the embodiment of FIGS. 7-10, the exemplary fan diffuser assembly 110 incorporating the ionization device 111 comprises an inverted frustoconical base 112 with rectangular base plate 114 and a high-speed electric fan 115. An exterior housing 120 covers the ionization device 111 and electric fan 115, and has a generally truncated pyramidal shape including a large rectangular intake end 121, tapered side walls 122, and a smaller rectangular output end 123. The intake end 121 of the housing 120 is longitudinally spaced from the base plate 114 and cooperates with the side walls 122 and frustoconical base 112 to define an air intake of the fan diffuser assembly 110. A perforated grill 125 is located at the output end 123 of the housing 120. In the present disclosure, the frustoconical base 112 and base plate 114, electric fan 115, housing 120 and grill 125 may be identical in both embodiments of the air diffuser assembly 10, 110.

As previously described, the exemplary frustoconical base 112 resides substantially within the exterior housing 120, and has opposing large and small diameter ends 131, 132, a tapering exterior 134 between the two ends 131, 132, and four circumferentially spaced assembly support posts 135. Each support post 135 extends longitudinally from the large diameter end 131 of the frustoconical base 112 to the small diameter end 132, and comprises an integrally formed radial web 136 for added stability and reinforcement. The electric fan 115 is operatively held within a square frame 141 carried by an assembly mounting plate 142 located adjacent the small diameter end 132 of the frustoconical base 112. The assembly mounting plate 142 attaches to interior corner mounts 145 of the housing 120 using fasteners 146 through aligned holes 147 and 148, and defines a circular plate opening 149 of a size corresponding substantially to an axial diameter of the fan 115. The exemplary fan 115 comprises an electric motor (not shown), a rotatable center hub 151 and a number of attached blades 152. The diameter of hub 151 corresponds substantially to the diameter of the frustoconical base 112 at its small diameter end 132.

Figure 8:
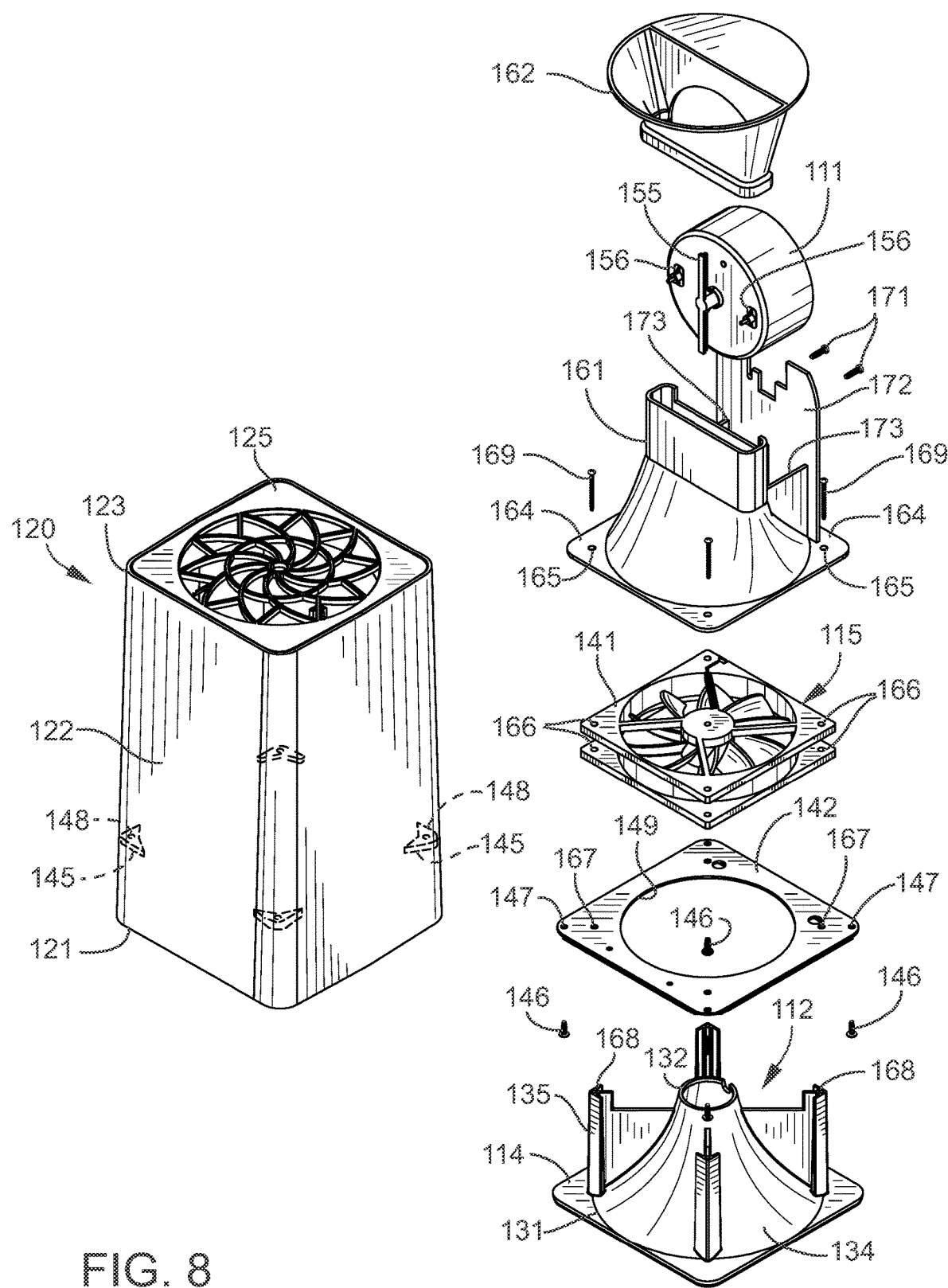
FIG. 8 is an exploded perspective view of the exemplary fan diffuser assembly.
Figure 9:
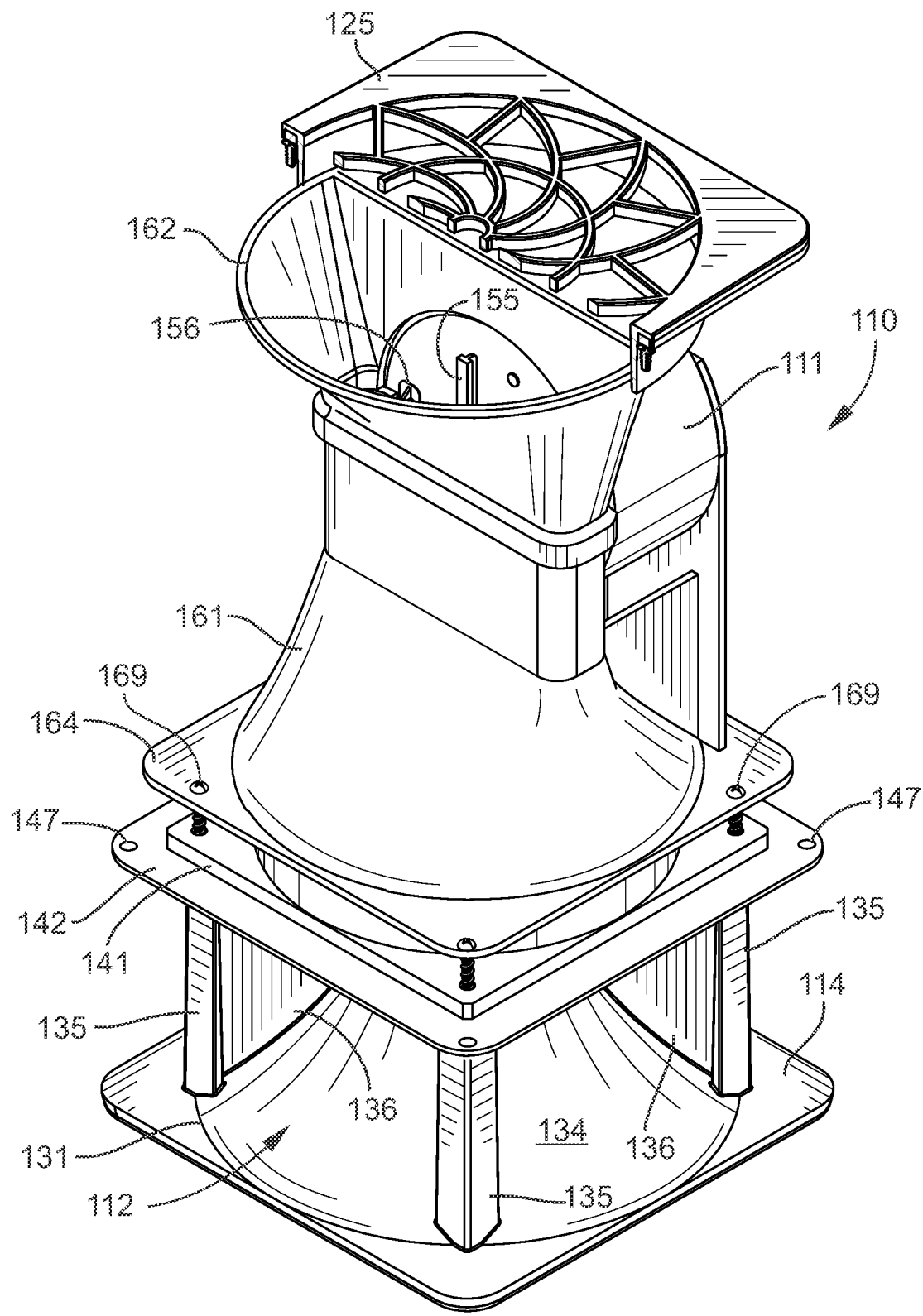
FIG. 9 is a further perspective view of the exemplary fan assembly with parts removed and shown in cross-section.
Figure 10:
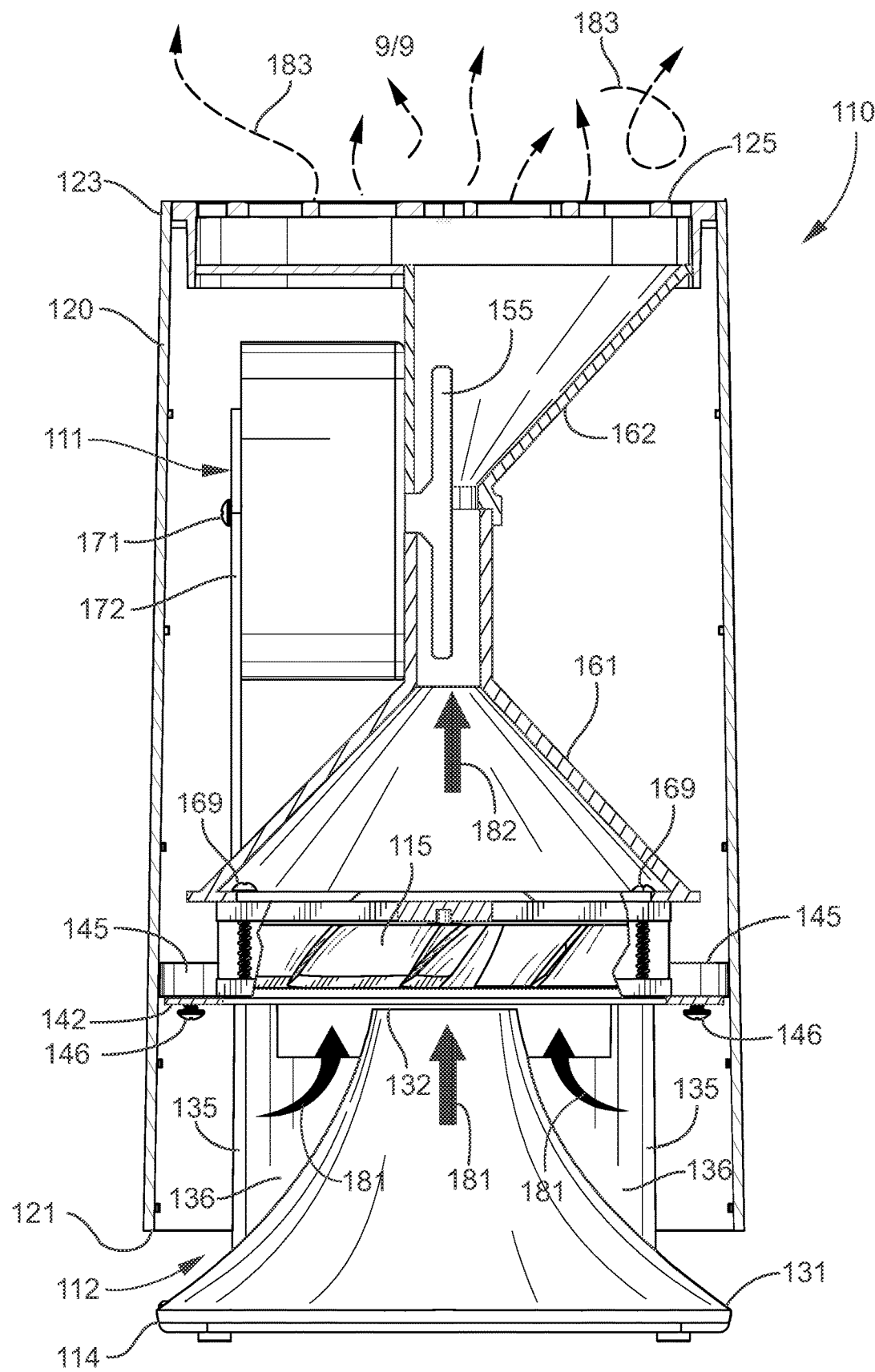
FIG. 10 is a side elevation of the exemplary fan diffuser assembly with parts shown in cross-section and direction arrows to demonstrate airflow into and through the assembly.

The exemplary ionization device 111 operates in a conventional manner using component parts standard in prior art needlepoint bipolar ion generators. As best shown in FIGS. 8, 9 and 10, such parts include, for example, an elongated rotational cleaning apparatus 155 spaced apart ion terminals and electrodes 156, and a DC stepper motor (not shown). The ionization device 111 is secured inside the housing 120 between opposing lower and upper air funnels 161, 162. The lower air funnel 161 has integrally formed mounting ears 164 with respective fastener holes 165 longitudinally aligned with corresponding fasteners holes 166, 167, 168 formed in the square frame 141 of the fan 115, assembly mounting plate 142, and support posts 135. Respective fasteners 169 are inserted through the aligned holes 165-168 to join the assembled parts together. Referring to FIGS. 8 and 10, the ionization device 111 is attached by fasteners 171 to a longitudinal mounting wall 172 integrally or separately formed with the lower funnel 161, and is carried by spaced apart web supports 173 such that the rotational cleaning apparatus 155 and ion terminals and electrodes 156 reside in a sealed space between the lower and upper funnels 161, 162.

As described in the '569 Patent referenced above, when the ionization device 111 is activated, it can generate approximately equal amounts of positive and negative ions, regardless of airflow velocity or other conditions such as humidity or temperature. In one example, the ionization device 111 produces positive ions and negative ions in a concentration of at least about 10 to the power of 9 (or 1000000000) ions/second, and operates on 24 VAC, 110 VAC or 200 VAC to 240 VAC without the use of an external transformer. In alternate embodiments, the ionization device 111 generates negative ions only, or positive ions only, or generates negative ions and positive ions in unequal quantities. The ionization device 111 may utilize nano-electronic components allowing it to be substantially compact, requiring less than 1 watt/ion generator module, for example, less than 0.5 watts/ion module, and in further examples, less than 0.36 watts per ion module. The device 111 may contain terminals for connecting the 24 VAC, 110-240 VAC, and neutral input.

Referring to FIG. 10, when activated the electric fan 115 generates a 360-degree laminar airflow into and through the air intake of the diffuser assembly 110. Laminar airflow enters the housing 120 at its intake end 121 and accelerates along the tapering exterior 134 of the frustoconical base 112, as indicated by direction arrows 181. The accelerated laminar airflow then passes through the rotating fan 115, as indicated by arrow 182, through the integrally joined lower and upper funnels 161, 162 and ionization device 111, and outwardly through the perforated grill 125, thereby releasing air-purifying positive and negative ions into the surrounding environment. The constriction at the joint between the lower and upper funnels 161, 162 increases the velocity of laminar airflow across the ion terminals and electrodes 156 (FIG. 8), while the expanding shape of the upper funnel 162 reduces the velocity as a more turbulent ionized airflow exits the housing 120 through the grill 125—as indicated by direction arrows 183. In the exemplary diffuser assembly 110, the electric fan 115 generates a volumetric airflow up to 500 CFM.

In each of the embodiments described above, the exemplary fan assembly 15, 115 operatively connects to an AC or DC power source, and comprises a printed circuit board assembly (PCBA) carrying electronics including a microcontroller unit with integrated Wi-Fi and Bluetooth, Wi-Fi and Bluetooth antennas, programming port, controls and manual switches for fan and LED lighting, battery backup, indicator lights for power, Wi-Fi and schedule, and others. In the exemplary assembly 110, the PCBA further comprises an ion control module.

For the purposes of describing and defining the present invention it is noted that the use of relative terms, such as "substantially", "generally", "approximately", and the like, are utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

Exemplary embodiments of the present invention are described above. No element, act, or instruction used in this description should be construed as important, necessary, critical, or essential to the invention unless explicitly described as such. Although only a few of the exemplary embodiments have been described in detail herein, those skilled in the art will readily appreciate that many modifications are possible in these exemplary embodiments without materially departing from the novel teachings and advantages of this invention. Accordingly, all such modifications are intended to be included within the scope of this invention as defined in the appended claims.

In the claims, any means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. Unless the exact language "means for" (performing a particular function or step) is recited in the claims, a construction under 35 U.S.C. § 112(f) [or 6th paragraph/pre-AIA] is not intended. Additionally, it is not intended that the scope of patent protection afforded the present invention be defined by reading into any claim a limitation found herein that does not explicitly appear in the claim itself.

What is claimed:
1. A fan diffuser assembly, comprising:
   an inverted frustoconical base having a large diameter end and an opposing small diameter end, and a plurality of spaced apart radial webs extending longitudinally between said large diameter end and said small diameter end;
   a housing located over said frustoconical base and carried by a respective support structure at each of said radial webs, and said housing comprising an intake end, side walls and an output end, and said intake end being longitudinally spaced apart from said large diameter end of said frustoconical base and cooperating with said side walls of said housing to define an air intake of said fan diffuser assembly;
   an electric fan located within said housing and mounted adjacent said small diameter end of said frustoconical base, whereby operation of said fan generates a 360-degree laminar airflow through said air intake, along a tapering exterior of said frustoconical base, through said housing and outwardly through said output end into a surrounding environment; and
   an air conditioning element located inside said housing between said electric fan and said output end of said housing.

2. The fan diffuser assembly according to claim 1, and comprising a cylindrical cartridge nest located inside said housing between said electric fan and said output end of said housing.

3. The fan diffuser assembly according to claim 2, wherein said air conditioning element comprises an exchangeable fragrance cartridge configured for being carried by said cartridge nest inside said housing.

4. The fan diffuser assembly according to claim 1, wherein said air conditioning element comprises an ionization device.

5. The fan diffuser assembly according to claim 4, wherein ionization device comprises a needlepoint bipolar ion generator.

6. The fan diffuser assembly according to claim 1, and comprising a removable perforated grill located at said output end of said housing.

7. The fan diffuser assembly according to claim 1, wherein said housing has a generally truncated pyramidal shape.

8. The fan diffuser assembly according to claim 1, wherein said intake end of said housing is rectangular.

9. The fan diffuser assembly according to claim 1, wherein said output end of said housing is rectangular.

10. The fan diffuser assembly according to claim 1, wherein said side walls of said housing are solid and continuous.

11. The fan diffuser assembly according to claim 1, wherein said support structures each comprise support posts integrally formed with respective radial webs and extending from said large diameter end to said small diameter end.

12. The fan diffuser assembly according to claim 1, and comprising an assembly mounting plate located between said frustoconical base and said electric fan, and defining a circular plate opening corresponding to an axial diameter of said electric fan.

13. The fan diffuser assembly according to claim 12, wherein said housing comprises a plurality of interior corner mounts for attaching said assembly mounting plate.

14. The fan diffuser assembly according to claim 1, wherein a diameter of said small diameter end of said frustoconical base end corresponds substantially to a hub diameter of said electric fan.

15. The fan diffuser assembly according to claim 1, wherein said large diameter end of said frustoconical base is greater than 3 times a diameter of said small diameter end of said frustoconical base.

16. The fan diffuser assembly according to claim 1, wherein a longitudinal distance between said large diameter end of said frustoconical base and said small diameter end of said frustoconical base is between 3-5 inches.

17. The fan diffuser assembly according to claim 1, wherein the tapering exterior of said frustoconical base between said large diameter end and said small diameter end has a curvature radius of between about 4-5 inches.

18. The fan diffuser assembly according to claim 1, wherein said electric fan generates a volumetric airflow of between 50 CFM and 500 CFM.

19. A fan diffuser assembly, comprising:
   an inverted frustoconical base having a large diameter end and an opposing small diameter end, and a plurality of spaced apart radial webs extending longitudinally between said large diameter end and said small diameter end;
   a housing located over said frustoconical base and carried by a respective support structure at each of said radial webs, and said housing comprising an intake end, side walls and an output end, and said intake end being longitudinally spaced apart from said large diameter end of said frustoconical base and cooperating with said side walls of said housing to define an air intake of said fan diffuser assembly;
   an electric fan located within said housing and mounted adjacent said small diameter end of said frustoconical base, whereby operation of said fan generates a 360-degree laminar airflow through said air intake, along a tapering exterior of said frustoconical base, through said housing and outwardly through said output end into a surrounding environment; and
   an exchangeable fragrance cartridge located inside said housing between said electric fan and said output end of said housing.

20. A fan diffuser assembly, comprising:
   an inverted frustoconical base having a large diameter end and an opposing small diameter end, and a plurality of spaced apart radial webs extending longitudinally between said large diameter end and said small diameter end, and wherein said large diameter end is greater than 3 times a diameter of said small diameter end;
   a housing located over said frustoconical base and carried by a respective support structure at each of said radial webs, and said housing comprising an intake end, side walls and an output end, and said intake end being longitudinally spaced apart from said large diameter end of said frustoconical base and cooperating with said side walls of said housing to define an air intake of said fan diffuser assembly;
   an electric fan located within said housing and mounted adjacent said small diameter end of said frustoconical base, whereby operation of said fan generates a 360-degree laminar airflow through said air intake, along a tapering exterior of said frustoconical base, through said housing and outwardly through said output end into a surrounding environment; and
   an ionization device located inside said housing between said electric fan and said output end of said housing.

* * * * *